United States Patent [19]

Kaiser

[11] Patent Number: 4,752,651

[45] Date of Patent: Jun. 21, 1988

[54] PRODUCTION OF LIGHT OLEFINS

[75] Inventor: Steven W. Kaiser, South Charleston, W. Va.

[73] Assignee: Union Carbide Corporation, Danbury, Conn.

[21] Appl. No.: 874,477

[22] Filed: Jun. 16, 1986

[51] Int. Cl.[4] .......................... C07C 1/20; C07C 1/32; C07C 1/26
[52] U.S. Cl. .................................... 585/640; 585/638
[58] Field of Search .................... 585/639, 640, 469

[56] References Cited

U.S. PATENT DOCUMENTS

| | | | |
|---|---|---|---|
| 4,499,327 | 2/1985 | Kaiser | 585/640 |
| 4,524,234 | 6/1985 | Kaiser | 585/640 |
| 4,554,143 | 11/1985 | Messina et al. | 423/306 |
| 4,567,029 | 1/1986 | Wilson et al. | 423/306 |
| 4,619,818 | 10/1986 | Derouane et al. | 423/306 |
| 4,623,527 | 11/1986 | Derouane et al. | 423/306 |
| 4,677,242 | 6/1987 | Kaiser | 585/638 |
| 4,677,243 | 6/1987 | Kaiser | 585/638 |
| 4,683,217 | 7/1987 | Lok et al. | 502/214 |
| 4,684,617 | 8/1987 | Lok et al. | 502/214 |
| 4,686,092 | 8/1987 | Lok et al. | 502/214 |
| 4,686,093 | 8/1987 | Flanigen et al. | 502/214 |

*Primary Examiner*—Asok Pal
*Attorney, Agent, or Firm*—Gerald L. Coon

[57] ABSTRACT

The process for the production of light olefins from a feedstock comprising at least an aliphatic hetero compound comprising contacting said feedstock in the presence of an aromatic diluent with a non-zeolitic molecular sieve at effective process conditions to produce light olefins.

32 Claims, No Drawings

PRODUCTION OF LIGHT OLEFINS

FIELD OF THE INVENTION

The present invention relates to a new catalytic process for the production of light olefins, i.e., olefins having not more than four carbon atoms, from a feedstock comprising aliphatic hetero compounds or mixtures thereof in the presence of a non-zeolitic molecular sieve catalyst.

BACKGROUND OF THE INVENTION

As a result of the limited availability and high cost of petroleum sources the cost of producing chemicals from such petroleum sources has been steadily increasing. Further, many in the chemical industry, as well as elsewhere, have raised the dire prediction of significant oil shortages in the not too distant future. As a result, the search for an alternative, low cost and more readily available raw material for chemical synthesis has been intense with the ultimate goal being the derivation of valuable chemical products from non-petroleum sources.

Such readily available sources are methanol, ethanol and their derivatives which may be manufactured from non-petroleum sources such as by fermentation or from synthesis gas, i.e., a mixture of oxides of carbon and hydrogen. Synthesis gas may be derived by the combustion of any carbonaceous material including coal, or any organic material, such as hydrocarbons, carbohydrates and the like. Thus, the use of methanol and its derivatives to form chemical products is particularly desirable in providing such a non-petroleum based route. The manufacture of methanol from synthesis gas by a heterogeneous catalytic reaction is presently an efficient commercial process.

Although methanol and its derivatives have for some time been considered as desirable starting materials for the manufacture of chemicals (which it is, e.g., in the manufacture of formaldehyde), the use of such as a replacement for petroleum or natural gas in commercial chemical syntheses has not been vast. If processes can be developed for the use of methanol and its derivatives for the commercial manufacture in large volume of chemical products or intermediates then the present dependence on petroleum sources as the basic raw material for chemical synthesis may be substantially lessened.

One proposed way to use methanol and its derivatives to manufacture chemical products is by catalytically converting them with crystalline aluminosilicate zeolites. Representative of the various contemplated processes using such crystalline aluminosilicate zeolites, and as more completely discussed hereinafter, are those processes disclosed in U.S. Pat. Nos.: 3,894,107; 4,046,825; 4,062,905; 4,079,095; 4,079,096; 3,911,041; and 4,049,573. What appears to be evident from the above patents, as well as other patents, is that the process is tied to the particular catalyst employed yielding differences in: product ratios (as well as by-product formation); catalyst life; conversion to product; selectivity to product; catalyst attrition; and the effects from additives to the catalytic process. The significance of these differences is readily apparent by reviewing the divergent results of the published art wherein various catalysts have been employed for the conversion of methanol to light olefin products. Representative of this art are: European Application No. 6,501 (catalyst is HZSM-5); European application No. 2,492 (catalyst is Mn exchanged 13X zeolite); German Offen. No. 2,909,928 (catalyst is Fe exchanged Silicalite); Agnew. Chem. Int. Ed., 19, 2 (1980), 126–7 (catalyst is Mn exchanged Chabazite and erionite); South African No. 78/2527 (catalyst is CaH-Fu-1 zeolite); and European Application No. 11,900 (catalyst is boron modified silica).

For example, German Offen. No. 2,909,928 discloses a 95–100 percent conversion with 5.2 weight percent of the product as ethylene, whereas the publication Agnew. Chem. Int. Ed., 19, 2 (1980), 126–7 discloses a conversion of about 82 percent with 35.7 weight percent of the product as ethylene.

A brief discussion of selected patents and publications will further serve to point out differences involved in the conversion of methanol and derivatives thereof to light olefin products.

U.S. Pat. No. 4,062,905 discloses a process for the conversion of methanol, dimethyl ether or mixtures thereof to hydrocarbon products rich in ethylene and propylene using a catalyst comprising a crystalline aluminosilicate zeolite characterized by pores, the major dimension of which, are less than 6 Angstroms, the pores being further characterized by pore windows of about a size as would be provided by 8-membered rings of oxygen atoms. The process is alleged to have the capability under certain conditions of producing less than 20 weight percent methane by weight of the hydrocarbon product. The claimed correlation in the patent between pore size, process conditions and the level of methane production is admittedly specifically limited to the crystalline aluminosilicate zeolites, see the quote below.

The passage beginning at column 3, line 5 (also see Example 17) of U.S. Pat. No. 4,062,905 demonstrates this view:

"In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5A, while satisfying the pore size requirements for zeolites useful as catalysts in the process described herein, is nevertheless, not a particularly feasible catalyst since under the conversion conditions utilized in such process, this zeolite produces considerable amounts of methane, i.e., far in excess of the specified maximum of 20 weight percent characterizing the crystalline aluminosilicate zeolites which have been found to be effective in selectively converting methanol and/or dimethyl ether to ethylene and propylene."

Even when a crystalline aluminosilicate zeolite having the desired physical and chemical properties is employed it may not be useful as a catalyst according to the patent's process. Thus, this patent discloses that the chemical composition of an aluminosilicate which has a desirable pore size may or may not be determinative as to whether it will produce methane at a given rate such that less than 20 percent by weight methane is produced.

The specificity of the catalysts in this field is demonstrated by U.S. Pat. Nos. 4,079,096 and 4,079,095 which disclose processes for the conversion of methanol, dimethyl ether or mixtures thereof to hydrocarbon products, such as ethylene and propylene, by contacting them with a catalyst comprising, respectively, a crystalline aluminosilicate zeolite of the erionite-offretite family and, the particular erionite-offretite of the crystalline aluminosilicate zeolite ZSM-34. The processes are limited to the use of crystalline aluminosilicates having substantially the same diffraction pattern as the erionite-offretite family.

U.S. Pat. No. 3,911,041 describes the conversion of methanol or dimethyl ether by contacting them with a crystalline aluminosilicate zeolite having a silica to alumina ratio of at least about 12, a constraint index of about 1 to 12, and containing phosphorous deposited on the crystal structure thereof in an amount of at least about 0.78 percent by weight. The phosphorous is disclosed as not in the framework of the crystalline aluminosilicate, as can be determined from the preparation procedure beginning at column 7, line 56 of the patent. The procedure set forth in the patent details that the crystalline aluminosilicate zeolite is formed prior to the addition of the phosphorus-containing compound, after which the phosphorous-containing compound is "reacted" with the surface sites of the zeolite to provide a surface treated material. Further, X-ray diffraction analyses of the zeolite before and after treatment with a phosphorus-containing compound showed substantially identical interplanar spacings (see Column 8, lines 54 to 64) indicating that no phosphorus was present in the framework. The surface treatment of the crystalline aluminosilicates is predicated on the patentees' belief that the number and strength of the aluminosilicates acid sites is related to the activity.

U.S. Pat. No. 4,049,573 describes a crystalline aluminosilicate zeolite having a silica to alumina ratio of at least 12 and a constraint index within the approximate range of 1 to 12, and having deposited thereon (as one of several possibilities) between about 0.25 and about 10 percent by weight of phosphorus oxide in combination with between about 0.25 and about 5 percent by weight of boron oxide and between about 2 and about 15 percent by weight of magnesium oxide. As was the case in the above-discussed U.S. Pat. No. 3,911,041, the phosphorous oxide, boron oxide and magnesium oxide are not incorporated into the zeolite framework but, instead, are added to the zeolite after the framework of the aluminosilicate zeolite has been formed, i.e., are provided as a post treatment of the aluminosilicate zeolite, apparently for the same reason.

As is evident from the above, the interest in selective catalysts for the manufacture of light olefins from methanol has been achieved from a special aluminosilicate structure or by achieving modifications of aluminosilicates by deposition with special additives. As above-noted, one of these was to deposit a phosphorous-containing compound (termed "doping" herein) in combination with a number of other compounds on an aluminosilicate zeolite.

U.S. Pat. Nos. 3,911,041 and 4,049,573, reports the sorption of phosphate ions onto amorphous metal oxides and combinations of metal oxides. Such sorptions of phosphate ions has been intensively studied in such areas as in the chemistry of soil, although such studies have not heretofore reported a crystalline microporous phosphate-containing material. For example, see: S. S. S. Rajan and K. W. Perrott, J. Soil Sci., 26, 257 (1975); J. A. Veith and G. Sposito, Soil. Sci., Soc. Am. J., 41, 870 (1977); E. A. Ferreiro and S. G. DeBussetto, Agrochimica, 24,184 (1980).

It has been reported (D. McConnell, Ameri. Min., 37, 609 (1952)) that certain natural aluminosilicate zeolites may have $PO_2^+$ substitution into the tetrahedral framework with such a substitution being reported in viseite which is considered to be isostructural with analcime. D. McConnell reported an elemental composition of:

$$5 CaO:5Al_2O_3:3SiO_2:3P_2O_5:n\ H_2O.$$

This report should be viewed cautiously, if not with skepticism, in view of the considerable question of agreement on the X-ray powder diffraction patterns of such a substituted viseite and analcime owing to the highly defective structure (with dangling —OH groups wherever tetrahedral cation vacancies occur) resorted to in order to substantiate such structures as being isostructural.

R. M. Barrer and D. J. Marshall (J. Chem. Soc., 1965, 6616 and 6621) reported the attempted substitution of phosphorus in aluminosilicates during hydrothermal crystallizations in the system, in respect to the following:

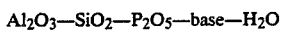

$$Al_2O_3—SiO_2—P_2O_5—base—H_2O$$

Although phosphate was observed to co-precipitate with the aluminosilicates in this system there was no evidence that an aluminosilicophosphate framework had formed.

R. M. Barre and M. Liguornick (J. Chem. Soc., Dalton Trans., 2126 (1974)) reported that by use of metakaolinite and phosphoric acid, and in some instances by further addition of silica, that zeolites were formed having an extremely low content of phosphorous with a maximum of 0.0117 atoms of phosphorus present per atom of aluminum. The authors explanation for this very low phosphorous content is that phosphate anions were trapped in cavities within the zeolite framework rather than actually being in the framework.

U.S Pat. No. 3,443,892 discloses a process for making Zeolite X by mixing aluminum phosphate with hot sodium silicate to give an as-synthesized product having the general formula:

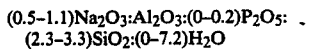

$$(0.5-1.1)Na_2O_3:Al_2O_3:(0-0.2)P_2O_5:\\(2.3-3.3)SiO_2:(0-7.2)H_2O$$

No chemical data is disclosed by the patentee for determining the framework structure and the patent reguires that the ratio of $SiO_2$ to $Na_2O$ in the reaction mixture must be less than 1.

The synthesis of aluminosilicophosphate zeolite analogues having phosphorus incorporated into the tetrahedral sites of the zeolite-type framework during hydrothermal synthesis employing substantial amounts of alkali metal cations has been reported by E. M. Flanigen and R. W. Grose at Advances in Chem., Series No. 101 pages 76–101 (1971). (Also see: Canadian Patent No. 911,410, issued Oct. 3, 1972 to Robert W. Grose and Edith M. Flanigen) In this report the authors reported compositions with the following types of zeolite-type frameworks: analcime, chabazite, phillipsite-harmotome, Type A zeolite, Type L zeolite, and Type B (P) zeolite. These compositions were reported to contain between 5 and 25 percent by weight $P_2O_5$ incorporated into the zeolite-type frameworks. The substitution of phosphorus for silicon did not appear to impart beneficial properties to the compositions not possessed by analogous aluminosilicate compositions, although differences were reported in some of the compositions, e.g., reduced adsorption capacity and reduced thermal stability on thermal activation. Many of the physical and chemical properties of the phosphorus-substituted analogues were inferior to those of the unsubstituted species.

U.S. Pat. No. 4,440,871 discloses a novel family of silicoaluminophosphates (SAPOs) and U.S. Pat. No. 4,449,327 discloses a process employing the SAPOs of U.S. Pat. No. 4,440,871 for the conversion of methanol, dimethyl ether, etc., to light olefins.

DISCLOSURE OF THE INVENTION

This invention comprises a process for the catalytic conversion of a feedstock comprising one or more aliphatic hetero compounds comprising alcohols, halides, mercaptans, sulfides, amines, ethers and carbonyl compounds or mixtures thereof to a hydrocarbon product containing light olefinic products, i.e., $C_2$, $C_3$ and/or $C_4$ olefins. The feedstock is contacted with a non-zeolitic molecular sieve (as hereinafter defined) at effective process conditions to produce light olefins. The process is preferably carried out in the presence of a diluent that is correlated to the selected non-zeolitic molecular sieve such that the average kinetic diameter of the diluent is greater than the median pore size of the non-zeolitic molecular sieve.

It has been found that non-zeolitic molecular sieves (denominated "NZMSs") are efficient catalysts for the conversion of a feedstock comprising aliphatic hetero compounds, preferably methanol, ethanol, dimethyl ether, diethyl ether or mixtures thereof, to light olefins and that the two carbon, three carbon, and four carbon ($C_2$–$C_4$) light olefin product content of the hydrocarbon reaction products generally comprises a major portion of the hydrocarbon products while methane and aromatics (other than the diluent) typically comprise a minor portion thereof.

DESCRIPTION OF THE INVENTION

The instant process relates to making light olefins containing 2 to 4 carbon atoms wherein said process comprises contacting a feedstock with a non-zeolitic molecular sieve as described hereinafter:

NON-ZEOLITIC MOLECULAR SIEVES ("NZMS")

The term "non-zeolitic molecular sieves" or "NZMS" is defined in the instant invention to include "ELAPSO" molecular sieves as disclosed in U.S. Ser. No. 600,312, filed Apr. 13, 1984 and certain "MeAPO", "FeAPO", "TAPO" and "ELAPO" molecular sieves, as hereinafter described. Crystalline metal aluminophosphates (MeAPOs where "Me" is at least one of Mg, Mn, Co and Zn) are disclosed in U.S. Pat. No. 4,567,029, issued Jan. 28, 1986; crystalline ferroaluminophosphates (FeAPOs) are disclosed in U.S. Pat. No. 4,554,143, issued Nov. 19, 1985; titanium aluminophosphates (TAPOs) are disclosed in U.S. Pat. No. 4,500,651, issued Feb. 19, 1985; certain non-zeolitic molecular sieves ("ELAPO") are disclosed in EPC Application No. 85104386.9 (Publication No. 0158976, published Oct. 13, 1985 and 85104388.5 (Publication No. 158349, published Oct. 16, 1985); and ELAPSO molecular sieves are disclosed in copending U.S. Ser. No. 600,312, filed Apr. 13, 1984 (EPC Publication No. 0159624, published Oct. 30, 1985). The aforementioned applications and patents are incorporated herein by reference thereto. The nomenclature employed herein to refer to the members of the aforementioned NZMSs is consistent with that employed in the aforementioned applications or patents. A particular member of a class is generally referred to as a "—n" species wherein "n" is an integer, e.g., MeAPO-11, MeAPO-31 and ELAPSO-31. In the following discussion on NZMSs set forth hereinafter the mole fraction of the NZMSs are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC Publication No. 0159,624, published Oct. 30, 1985, incorporated herein by reference) as crystalline molecular sieves having three-dimensional microporous framework structures of $ELO_2$, $AlO_2$, $PO_2$, $SiO_2$ oxide units and having an empirical chemical composition on an anhydrous basis expressed by the formula:

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a three dimensional oxide framework, "EL" is characterized as an element having a mean "T-O" distance in tetrahedral oxide structures between about 1.51 Angstroms and about 2.06 Angstroms, "EL" has a cation electronegativity between about 125 kcal/g-atom to about 310 kcal/m-atom and "EL" is capable of forming stable M—O—P, M—O—Al or M—O—M bonds in crystalline three dimensional oxide structures having a "M—O" bond dissociation energy greater than about 59 kcal/g-atom at 298° K.; and "w", "x", "y" and "z" represent the mole fractions of "EL", aluminum, phosphorus and silicon, respectively, present as framework oxides said mole fractions being within the limiting compositional values or points as follows:

| Point | Mole Fraction | | |
|---|---|---|---|
| | x | y | (z + w) |
| A | 0.60 | 0.39 − (0.01)p | 0.01 (p + 1) |
| B | 0.39 − (0.01p) | 0.60 | 0.01 (p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "El" in the $(El_wAl_xP_ySi_z)O_2$ constituent.

The "ELAPSO" molecular sieves are also described as crystalline molecular sieves having three-dimensional microporous framework structures of $ELO_2$, $AlO_2$, $SiO_2$ and $PO_2$ tetrahedral oxide units and having an empirical chemical composition on an anhydrous basis expressed by the formula:

wherein "R" represents at least one organic templating agent present in the intracrystalline pore system; "m" represents the molar amount of "R" present per mole of $(El_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides said mole fractions being within the limiting compositional values or points as follows:

| | Mole Fraction | | |
|---|---|---|---|
| Point | x | y | (z + w) |
| a | 0.60 | 0.39 − (0.01)p | 0.01 (p + 1) |
| b | 0.39 − (0.01p) | 0.60 | 0.01 (p + 1) |
| c | 0.10 | 0.55 | 0.35 |
| d | 0.55 | 0.10 | 0.35 | where "p" is as above defined.

The "ELAPSO" molecular sieves include numerous species which are intended herein to be within the scope of the term "non-zeolitic molecular sieves" such being disclosed in the following copending and commonly assigned applications, incorporated herein by reference thereto:

| U.S. Ser. No. | Filed | NZMS |
|---|---|---|
| 600,174 | April 13, 1984 | CoAPSO |
| 600,173 | April 13, 1984 | FeAPSO (now U.S. Pat. No. 4,683,217, issued July 28, 1987) |
| 600,180 | April 13, 1984 | MgAPSO |
| 600,175 | April 13, 1984 | MnAPSO (now U.S. Pat. No. 4,686,092, issued August 11, 1987) |
| 600,179 | April 13, 1984 | TiAPSO (now U.S. Pat. No. 4,684,617, issued August 4, 1987) |
| 600,170 | April 13, 1984 | ZnAPSO |
| 600,168 | April 13, 1984 | CoMgAPSO |
| 600,182 | April 13, 1984 | CoMnMgAPSO |
| 845,984 | March 31, 1986 | AsAPSO |
| 845,255 | March 28, 1986 | BAPSO |
| 841,752 | March 20, 1986 | BeAPSO |
| 852,174 | April 15, 1986 | CAPSO |
| 845,985 | March 31, 1986 | GaAPSO |
| 852,175 | April 15, 1986 | GeAPSO |
| 847,227 | April 12, 1986 | LiAPSO |

TiAPSO MOLECULAR SIEVES

The TiAPSO molecular sieves of U.S. Ser. No. 600,179, filed Apr. 13, 1984 have three-dimensional microporous framework structures of $TiO_2$, $AlO_2$, $PO_2$ and $SiO_2$ tetrahedral oxide units having an empirical chemical composition on an anhydrous basis expressed by the formula:

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined being within the limiting compositional values or points as follows:

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d, said points a, b, c and d representing the following values for "w", "x", "y" and "z":

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

TiAPSO compositions are generally synthesized by hydrothermal crystallization from a reaction mixture containing active resources of titanium, silicon, aluminum and phosphorus, and preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z) = 1.00$ mole. Molecular sieves containing titanium, aluminum, phosphorus and silicon as framework tetrahedral oxides are prepared as follows:

Preparative Reagents

TiAPSO compositions are typically prepared using numerous regents. Typical reagents which may be employed and abbreviations employed in U.S. Ser. No. 600,179 for such reagents are as follows:
(a) Alipro: aluminum isopropoxide;
(b) LUDOX-LS: LUDOX-LS is the tradename of DuPont for an agueous solution of 30 weight percent $SiO_2$ and 0.1 weight percent $Na_2O$;
(c) $H_3PO_4$: 85 weight percent aqueous phosphoric acid;
(d) Tiipro: titanium isopropoxide;
(e) TEAOH: 40 weight percent aqueous solution of tetraethylammonium hydroxide;
(f) $Pr_2NH$: di-n-propylamine, $(C_3H_7)_2NH$;
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

Preparative Procedures

TiAPSOs may be prepared by forming a starting reaction mixture by adding the $H_3PO_4$ and the water. This mixture is mixed and to this mixture aluminum isopropoxide is added. This mixture is then blended until a homogeneous mixture is observed. To this mixture the LUDOX-LS is added and the resulting mixture blended (about 2 minutes) until a homogeneous mixture is observed.

The titanium isopropoxide is added to the above mixture and the resulting mixture blended until a homogeneous mixture is observed. The organic templating agent is then added to the resulting mixture and the resulting mixture blended until a homogeneous mixture is observed, i.e., about 2 to 4 minutes. When the organic templating agent is quinuclidine the procedure is modified such that the quinuclidine is dissolved in about one half the water and accordingly the $H_3PO_4$ is mixed with about one half the water. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

The products are removed from the reaction vessel and cooled.

MgAPSO MOLECULAR SIEVES

The MgAPSO molecular sieves of U.S. Ser. No 600,180, filed Apr. 13, 1984 (EPC Publication No. 0 158 348, published Oct. 16, 1985), have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula:

wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:
(a) Alipro: aluminum isopropoxide;
(b) CATAPAL: Trademark of Condea for hydrated pseudoboehmite;
(c) LUDOX-LS: Trademark of DuPont for an aqueous solution of 30 weight percent $SiO_2$ and 0.1 weight percent $Na_2O$;
(d) $Mg(Ac)_2$: magnesium acetate tetrahydrate, $Mg(C_2H_3O_2)_2 \cdot 4H_2O$;
(e) $H_3PO_4$: 85 weight percent aqueous phosphoric acid in water;
(f) TBAOH: tetraethylammonium hydroxide (40 wt. % in water);
(g) $Pr_2NH$: di-n-propylamine;
(h) $Pr_3N$: tri-n-propylamine;
(i) Quin: Quinuclidine;
(j) MQuin: Methyl Quinuclidine hydroxide, (17.9% in water);
(k) C-hex: cyclohexylamine;
(l) TEAOH: tetraethylammonium hydroxide (40 wt. % in water);
(m) DEEA: Diethylethanolamine;
(n) i-$Pr_2NH$: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

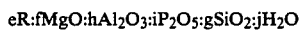

wherein e, f, g, h, i and j represent the moles of template R, magnesium (expressed as the oxide), $SiO_2$, $Al_2O_3$, $P_2O_5$ ($H_3PO_4$ expressed as $P_2O_5$) and $H_2O$, respectively.

The reaction mixtures may be prepared by the following representative procedures, designated hereinafter as Methods A, B and C.

Method A

The reaction mixture is prepared by mixing the ground aluminum source (Alipro or CATAPAL) with the $H_3PO_4$ and water on a gradual basis with occasional cooling with an ice bath. The resulting mixture is blended until a homogeneous mixture is observed. When the aluminum source is CATAPAL the water and $H_3PO_4$ is first mixed with the CATAPAL added thereto. The magnesium acetate is dissolved in portion of the water and is then added followed by addition of the LUDOX-LS. The combined mixture is blended until a homogenous mixture is observed. The organic templating agent is added to this mixture and blended until a homogenous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out at the autogenous pressure. The products are removed from the reaction vessel, cooled and evaluated as set forth hereinafter.

Method B

When method B is employed the organic templating agent is di-n-propylamine. The aluminum source, silicon source and one-half of the water are first mixed and blended until a homogeneous mixture is observed. A second solution was prepared by mixing the remaining water, the $H_3PO_4$ and the magnesium acetate. This solution is then added to the above mixture. The magnesium acetate and $H_3PO_4$ solution is then added to the above mixture and blended until a homogeneous mixture is observed. The organic templating agent(s) is then added and the resulting reaction mixture digested and product recovered as is done in Method A.

Method C

Method C is carried out by mixing aluminum isopropoxide, LUDOX LS and water in a blender or by mixing water and aluminum isopropoxide in a blender followed by addition of the LUDOX LS. $H_3PO_4$ and magnesium acetate are then added to this mixture. The organic templating agent is then added to the resulting mixture and digested and product recovered as is done in Method A.

MnAPSO MOLECULAR SIEVES

The MnAPSO molecular sieves of U.S. Ser. No. 600,175, filed Apr. 13, 1984 have a framework structrue of $MnO_2^{-2}$, $AlO_2^-$, $PO_2^+$, and $SiO_2$ tetrahedral units having an empirical chemical composition on an anhydrous basis expressed by the formula:

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MnAPSO compositions are generally synthesized by hydrothermal crystallization from a reaction mixture containing reactive sources of manganese, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days with generally from about 4 hours to about 20 days have been observed. The product is recovered by any convenient method such as centrifugation or filtration.

In synthesizing the MnAPSO compositions, it is preferred to employ a reaction mixture composition expressed in terms of the molar ratios as follows:

$aR:(Mn_wAl_xP_ySi_z)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing manganese, aluminum, phosphorus and silicon as framework tetrahedral oxide units are prepared as follows:

Preparative Reagents

MnAPSO compositions may be prepared by using numerous reagents. Reagents which may be employed to prepare MnAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) MnAc: Manganese acetate, $Mn(C_2H_3O_2)_2 \cdot 4H_2O$;
(f) TEAOH: 40 weight percent aqueous solution of tetraethylammonium hydroxide;
TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

Preparative Procedures

MnAPSOs are prepared by forming a starting reaction mixture by adding the $H_3PO_4$ to one half of the quantity of water. This mixture is mixed and to this mixture the aluminum isopropoxide or CATAPAL is added. This mixture is then blended until a homogeneous mixture is observed. To this mixture the LUDOX LS is added and the resulting mixture blended (about 2 minutes) until a homogeneous mixture is observed. A second mixture is prepared using the manganese acetate and the remainder (about 50%) of the water. The two mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

CoAPSO MOLECULAR SIEVES

The CoAPSO molecular sieves of U.S. Ser. No. 600,174, filed Apr. 13, 1984 (EPC Publication No. 0 161 489, published Nov. 21, 1985), have three-dimensional microporous framework structures of $CoO_2^{-2}$, $AlO_2^{-}$, $PO_2^{+}$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero a 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y", and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$$aR: (Co_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepared CoAPSOs include:
(a) Alipro: aluminum isoproproxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) $Co(Ac)_2$: cobalt acetate $Co(C_2H_3O_2)_2 \cdot 4H_2O$;
(e) $CoSO_4$: cobalt sulfate $(CoSO_4 \cdot 7H_2O)$;
(f) $H_3PO_4$: 85 weight percent phosphoric acid in water;
(g) TBAOH: tetrabutylammonium hydroxide (25 wt % in methanol);
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$;
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

$$eR:fCoO:hAl_2O_3:iP_2O_5:gSiO_2:jH_2O$$

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively.

The reaction mixtures are prepared by forming a starting reaction mixture comprising the $H_3PO_4$ and one half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., $Co(Ac)_2$, $Co(SO_4)$ or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984, (EPC Publication No. 0 158 975, published Oct. 23, 1985), comprise framework structures of $ZnO_2^{-2}$, $AlO_2^-$, $PO_2^+$ and $SiO_2$ tetrahedral units having an anhydrous basis expressed chemical composition on an anhydrous basis expressed by the formula:

mR: $(Zn_wAl_xP_ySi_z)O_2$ wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure-directing, agent, preferably a compound of an element or Group VA of the Periodic Table, and/or optionally an alkali of other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

In synthesizing the ZnAPSO compositions, it is preferred to employ a reaction mixture composition expressed in terms of the molar ratios as follows:

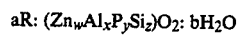

aR: $(Zn_wAl_xP_ySi_z)O_2$: $bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing zinc, aluminum, phosphorus and silicon as framework tetrahedral oxide units are prepared as follows:

Preparative Reagents

ZnAPSO compositions are typically prepared using numerous reagents. Reagents which may be employed to prepare ZnAPSOs include:
(a) Alipro: aluminum isopropoxide;
(b) LUDOX-LS: LUDOX LS is the trade name of DuPont for an aqueous solution of 30 weight percent $SiO_2$ and 0.1 weight percent $Na_2$;
(c) CATAPAL: Trademark of Condea Corporation for hydrated pseudoboehmite;
(d) $H_3PO_4$: 85 weight percent aqueous phosphoric acid;
(e) ZnAc: Zinc Acetate, $Zn(C_2H_3O_2)_2\cdot 4H_2O$;

(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH \cdot 5H_2O$;
(i) TPAOH: 40 weight percent aqueous solution of tetrapropylammonium hydroxide, $(C_3H_7)_4NOH$;
(j) $Pr_2NH$: di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

Preparative Procedure

ZnAPSO compositions are typically prepared by forming reaction mixtures having a molar composition expressed as:

$$eR:fZnO:gAl_2O_3:hP_2O_5:iSiO_2:jH_2O$$

wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively.

The reaction mixtures are generally prepared by forming a starting reaction mixture comprising the $H_3PO_4$ and a portion of the water. This mixture is stirred and the aluminum source added. The resulting mixture is blended until a homogeneous mixture is observed. The LUDOX LS is then added to the resulting mixture and the new mixture blended until a homogeneous mixture is observed. The zinc source (zinc acetate) is dissolved in the remaining water and combined with the first mixture. The combined mixture is blended until a homogenous mixture is observed. The organic templating agent is added to this mixture and blended for about two to four minutes until a homogenous mixture is observed. The resulting mixture (final reaction mixture) is placed in a lined (polytetrafluoroethylene) stainless steel pressure vessel and digested at an effective temperature for an effective time. Digestions are typically carried out at the autogenous pressure. The products are removed from the reaction vessel and cooled.

FeAPSO MOLECULAR SIEVES

The FeAPSO of U.S. Ser. No. 600,173, filed Apr. 13, 1984 have molecular sieves having a three dimensional microporous crystal framework structures of $FeO_2^{-2}$, (and/or $FeO_2^{-}$), $AlO_2^{-}$, $PO_2^{+}$ and $SiO_2$ tetrahedral oxide units and having a unit empirical formula, on an anhydrous basis, of:

$$mR:(Fe_wAl_xP_ySi_z)O_2 \qquad (1)$$

wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The FeAPSOs of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lined with an inert plastic material, such as polytetrafluoroethylene, and heated, preferably under the autogenous pressure, at an effective temperature which is generally between about 50° C., and about 250° C. and preferably between about 100° C. and 200° C. until crystals of the FeAPSO product are obtained, usually a period of from several hours to several weeks. Molecular sieves containing iron, aluminum phosphorus and silicon as framework tetrahedral oxide units are typically prepared as follows:

Preparative Reagents

FeAPSO compositions may be prepared using numerous reagents. Reagents which may employed to prepare FeAPSOs include:
(a) Alipro: aluminum isopropoxide, $Al(OCH(CH_3)_2)_3$;
(b) LUDOX-LS: LUDOX-LS is the trademark of Du Pont for an aqueous solution of 30 weight percent $SiO_2$ and 0.1 weight percent $Na_2O$;
(c) CATAPAL: trademark for hydrated aluminum oxide containing about 75 wt. percent $Al_2O_3$ (pseudoboehmite phase) and about 25 wt. percent water;
(d) $Fe(Ac)_2$: Iron (II) acetate;
(e) $FeSO_4$. Iron (II) sulfate hexahydrate;
(f) $H_3PO_4$: 85 weight percent phosphoric acid in water;
(g) TEAOH: 40 weight percent aqueous solution of tetraethylammonium hydroxide;
(h) TBAOH: 40 weight percent aqueous solution of tetrabutylammonium hydroxide;
(i) $Pr_2NH$: di-n-propylamine (($C_3H_7)_2NH$);
(j) $Pr_3N$: tri-n-propylamine (($C_3H_7)_3N$);
(k) Quin: Quinuclidine ($C_7H_{13}N$);
(l) MQuin: Methyl Quinuclidine hydroxide ($C_7H_{13}NCH_3OH$);
(m) TMAOH: tetramethylammonium hydroxide pentahydrate; and
(o) C-hex: cyclohexylamine.

(a) Reaction mixtures to prepare FeAPSOs are typically prepared by grinding an aluminum isopropoxide in a blender followed by slowly adding a $H_3PO_4$ solution with mixing. A solution/dispersion of iron acetate in water is added and then a silica (e.g., LUDOX-LS) is added. The organic templating agent is then added to this mixture, or in some cases one-half of this mixture, and the mixture blended to form a homogeneous mixture. For example, in one embodiment, the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2** |
| FeO* | 0.2 |
| TEAOH | 1.0 |
| H$_2$O | 50 |

*Iron (II) acetate reported as Iron (II) oxide.
**SiO$_2$ was 0.6 in examples 5C to 8C The reaction mixture is sealed in a stainless steel pressure vessel lined with polytetrafluoroethylene and heated in an oven at a temperature, time and at the autogenous pressure. The solid reaction product is recovered by filtration, washed with water and dried at room temperature.

In another embodiment, reaction mixtures are prepared by grinding the aluminum isopropoxide in a blender followed by addition of a solution/dispersion of iron (II) acetate. H$_3$PO$_4$ is added to this mixture and the resulting mixture blended to form a homogeneous mixture. A silica e.g., LUDOX-LS) is added to this mixture except that in some instances the silica may be added with the H$_3$PO$_4$. The resulting mixtures were blended until a homogeneous mixture is observed. Organic templating agent is added to each mixture and the resulting mixtures placed in a stainless steel pressure vessel lined with polytetrafluoroethylene and heated, washed and the product recovered. In this embodiment the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Template | 1.0 |
| H$_2$O | 50 |

*Iron (II) acetate reported as Iron (II) oxide.

CoMnAPSO MOLECULAR SIEVES

CoMnAPSO molecular sieves of U.S. Ser. No. 600,168, filed Apr. 13, 1984, (EPC Publication No. 0 158 350, published Oct. 16, 1985), may be expressed by the empirical chemical formula (anhydrous) as follows:

mR: (Co$_u$Mn$_v$Al$_x$P$_y$Si$_z$)O$_2$ where "u", "v", "x", "y" and "z" represent the mole. The CoMnAPSO molecular sieves have an empirical chemical composition on an anhydrous basis expressed by the formula:

mR: (Co$_u$Mn$_v$Al$_x$P$_y$Si$_z$)O$_2$ wherein "R" represents at least one organic templating agent present in the intracrystalline pore system; "m" represents the molar amount of "R" present per mole of (Co$_u$Mn$_v$Al$_x$P$_y$Si$_z$)O$_2$ from zero (0) to about 0.3; and "u", "v", "x", "y" and "z" represent the mole fractions of cobalt, manganese, aluminum, phosphorus and silicon, respectively, present as tetrahedral oxides. The mole fractions "u", "v", "x", "y", and "z" are generally defined as being within the limiting compositional values or points as follows, wherein "w", the combined mole fractions of manganese and cobalt, is the sum of "u" and "v":

| Point | Mole Fraction | | |
|---|---|---|---|
|  | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Preferably the mole fractions u, v, x, y and z will fall within the limiting compositional values or points as follows:

| Point | Mole Fraction | | |
|---|---|---|---|
|  | x | y | (z + w) |
| a | 0.55 | 0.42 | 0.03 |
| b | 0.42 | 0.55 | 0.03 |
| c | 0.10 | 0.55 | 0.35 |
| d | 0.55 | 0.10 | 0.35 |

CoMnAPSO compositions are generally synthesized by hydrothermal crystallization from a reaction mixture containing reactive sources of cobalt, manganese, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the CoMnAPSO product are obtained, usually over a period of from several hours to several weeks. Typical effective crystallization times are from about 2 hours to 30 days with from about 4 hours to about 20 days being generally employed to obtain CoMnAPSO products. The product is recovered by any convenient method such as centrifugation or filtration.

In synthesizing the CoMnAPSO compositions, it is preferred to employ a reaction mixture composition expressed in terms of the molar ratios as follows:

aR: (Co$_u$Mn$_v$Al$_x$P$_y$Si$_z$)O$_2$: bH$_2$O wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "u", "v", "x", "y", and "z" represent the mole fractions of elements cobalt, manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.37 | 0.03 |
| G | 0.37 | 0.60 | 0.03 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "u", "v", "x", "y" and "z" such that (u+v+x+y+z)=1.00 mole. CoMnAPSO compositions were prepared using numerous regents.

Reagents which may be employed to prepare CoMnAPSOs include:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent phosphoric acid;
(d) MnAc: Manganese acetate, $Mn(C_2H_3O_2)_2 \cdot 4H_2O$;
(e) CoAc: Cobalt Acetate, $Co(C_2H_3O_2)_2 \cdot 4H_2O$;
(f) TEAOH: 40 weight percent aqueous solution of tetraethylammonium hydroxide; and
(g) $Pr_2NH$: di-n-propylamine, $(C_3H_7)_2NH$.

Preparative Procedures

CoMnAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate and one half of the remaining water. A third mixture is prepared using cobalt acetate and one half of the remaining water. The three mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. The pH of the mixture is measured and adjusted for temperature. The mixture is then placed in a lined (polytetrafluoroethylene) stainless steel pressure vessel and digested at a temperature. Digestions are typically carried out at the autogenous pressure.

CoMnMgAPSO MOLECULAR SIEVES

The CoMnMgAPSO molecular sieves of U.S. Ser. No. 600,182, filed April 13, 1984 have three-dimensional microporous framework structures of $CoO_2^{-2}$, $MnO_2^{-2}$, $MgO_2^{-2}$, $AlO_2^-$, $PO_2^+$ and $SiO_2$ tetrahedral oxide units and have an empirical chemical composition on an anhydrous basis expressed by the formula:

wherein "R" represents at least one organic templating agent present in the intracrystalline pore system; "m" represents the molar amount of "R" present per mole of $(Co_tMn_uMg_vAl_xP_ySi_z)O_2$, and has a value of from zero to about 0.3; and "t", "u", "v", "x", "y" and "z" represent the mole fractions of cobalt, manganese, magnesium, aluminum, phosphorus and silicon, respectively, present as tetrahedral oxides, each having a value of at least 0.01. The mole fractions "t", "u", "v", "x", "y" and "z" are generally defined as being within the limiting compositional values or points as follows, wherein "w", the combined mole fractions of cobalt, manganese and magnesium, is the sum of "t", "u" and "v":

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure-directing, agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each has a value of at least 0.01.

In a preferred embodiment the reaction mixture is selected such that the mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that $(t+u+v+x+y+z)=1.00$ mole. Molecular sieves containing cobalt, manganese, magnesium, aluminum, phosphorus and silicon as framework tetrahedral oxide units are prepared as follows:

Preparative Reagents

CoMnMgAPSO compositions may be prepared by numerous reagents. Reagents which may be employed to prepare CoMnAPSOs include:
(a) Alipro: aluminum isopropoxide;
(b) LUDOX-LS: LUDOX-LS is the tradename of Du Pont for an aqueous solution of 30 weight percent $SiO_2$ and 0.1 weight percent $Na_2O$;
(c) $H_3PO_4$: aqueous solution which is 85 weight percent phosphoric acid;
(d) MnAc: Manganese acetate, $Mn(C_2H_3O_2)_2 \cdot 4H_2O$;
(e) CoAc: Cobalt Acetate, $Co(C_2H_3O_2)_2 \cdot 4H_2O$;
(f) MgAc: Magnesium Acetate $Mg(C_2H_3O_2) \cdot 4H_2O$;
(g) TEAOH: 40 weight percent aqueous solution of tetraethylammonium hydroxide; and
(h) $Pr_2NH$: di-n-propylamine, $(C_3H_7)_2NH$.

Preparative Procedures

CoMnMgAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate using one third of the remainder of the water for each mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at a temperature for a time. Digestions are typically carried out at the autogenous pressure.

MeAOP MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three-dimensional microporous crystal framework structure of $MO_2^{-2}$, $AlO_2^-$ and $PO_2^+$ tetrahedral units and have an essential empirical chemical composition, on an anhydrous basis, of:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3 maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product be a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing such compositions, the "short hand" reference "MeAPO" is employed hereinafter. Also in those cases where the metal "Me" in the composition is magnesium, the acronym MAPO is applied to the composition. Similarly, ZAPO, MnAPO, and CoAPO are applied to the compositions which contain zinc, manganese and cobalt, respectively.

To identify the various structural species which make up each of the subgeneric classes MAPO, ZAPO, CoAPO and MnAPO, each species is assigned a number and is identified, for example, as ZAPO-5, MAPO-11, CoAPO 11 and so forth.

The term "essential empirical chemical composition" is meant to include the crystal framework and can include any organic templating agent present in the pore system, but does not include alkali metal or other ions which can be present by virtue of being contained in the reaction mixture or as a result of post synthesis ion-exchange. Such ionic species, when present, function primarily as charge-balancing ions for $AlO_2^-$ and/or $MO_2^{-2}$ tetrahedra not associated $PO_2^+$ tetrahedra or an organic ion derived with PO2 from the organic templating agent.

The metal aluminophosphates ("MeAPOs") are synthesized by hydrothermal crystallization from a reaction mixture containing reactive sources of the metal "M", alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C. until crystals of the metal aluminophosphate product are obtained, usually a period of from 4 hours to 2 weeks. The product is recovered by any convenient method such as centrifugation or filtration.

In synthesizing the MeAPO compositions, it is preferred to employ a reaction mixture composition expressed in terms of molar ratios as follows:

$$aR:(M_xAl_yP_z)O_2:bH_2O$$

wherein "R" is an organic templating agent; "a" has a value great enough to constitute an effective concentration of "R" and is within the ranghe of >0 to 6; "b" has a value of from zero to 500, preferably 2 to 30; "M" represents a metal of the roup zinc, magnesium, manganese and cobalt, "x", "y" and "z" represent the mole fractions, respectively, of "M", aluminum and phosphorus in the $(M_xAl_yP_z)O_2$ constituent, and each has a value of at least 0.01, the said points E, F, G, H, I, and J representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole.

In forming the reaction mixture from which the metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N-N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The preferred phosphorus source is phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, magnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like.

While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular MeAPO species. As a general rule, the templating agent, and hence the occluded organic species, is too large to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the MeAPO phase wherein the organic moiety occupying the intracrystalline pore system as a result of the hydrothermal crystallization process has been reduced by post synthesis treatment such that the value of "m" in the composition formula:

$mR:(M_xAl_yP_z)O_2$ has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized MeAPO material.

Since the MeAPO compositions are formed from AlO2, PO2, and MO2 tetrahedral units which, respectively, have a net charge of −1, +1, and −2, the matter of cation exchangeability is considerably more complicated than in the case of zeolitic molecular sieves in which, ideally, there is a stoichiometric relationship between AlO2 tetrahedra and charge-balancing cations. In the MeAPO compositions, an AlO2− tetrahedron can be balanced electrically either by association with a PO2+ tetrahedron or a simple cation such as an alkali metal cation, a cation of the metal "M" present in the reaction mixture, or an organic cation derived from the templating agent. Similarly an MO2−2 tetrahedron can be balanced electrically by association with PO2+ tetrahedra, a cation of the metal "M", organic cations derived from the templating agent, or other divalent or polyvalent metal cations introduced from an extraneous source. It has also been postulated that non-adjacent AlO2− and PO2+ tetrahedral pairs can be balanced by Na+ and OH−, respectively [Flanigen and Grose, Molecular Sieve Zeolites-I, ACS, Washington, D.C. (1971)].

FAPO MOLECULAR SIEVES

Ferroaluminophosphates are disclosed in U.S. Pat. No. 4,554,143, incorporated herein by reference, and have a three-dimensional microporous crystal framework structure of AlO2, FeO2, and PO2 tetrahedral units and have an essential empirical chemical composition, on an anhydrous basis, of:

$mR:(Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3 maximum value in each case depending upon the molecular dimensions of the templating agent and the available void volume of the pore system of the particular ferroaluminophosphate involved; "x", "y", and "z" represent the mole fractions of iron, aluminum and phosphorus, respectively, present as tetrahedral oxides, representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the FeO2 structural units can be in either the ferric or ferrous valence state, depending largely upon the source of the iron in the synthesis gel. Thus, an FeO2 tetrahedron in the structure can have a net charge of either −1 or −2. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in some as yet undetermined form, and may or may not be structurally significant.

For convenience in describing the ferroaluminophosphates, the "short hand" acronym "FAPO" is sometimes employed hereinafter. To identify the various structural species which make up the generic class FAPO, each species is assigned a number and is identified, for example, as FAPO-11, FAPO-31 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $FeO_2^-$ and/or $AlO_2^{-2}$ tetrahedra, $FeO_2^{-2}$ tetrahedra associated with $PO_2^+$ tetrahedra or not associated with $PO_2^+$ tetrahedra or an organic ion derived from the organic templating agent.

The aforesaid ferroaluminophosphates are synthesized by hydrothermal crystallization from a reaction mixture containing reactive sources of iron oxide, alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature of at least 100° C., and preferably between 100° C. and 250° C. until crystals of the metal aluminophosphate product are obtained, usually a period of from 2 hours to 2 weeks. The product is recovered by any convenient method such as centrifugation or filtration.

In synthesizing the FAPO compositions, it is preferred to employ a reaction mixture composition expressed in terms of molar ratios as follows:

$$aR:(Fe_xAl_yP_z)O_2:bH_2O$$

wherein "R" is an organic templating agent; "a" has a value great enough to constitute an effective concentration of "R" and is within the range of >0 to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value of at least 0.01, and representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(Fe+Al+P)=(x+y+z)=1.00$ mole.

In forming the reaction mixture from which the ferroaluminophosphates are crystallized, the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tri-n-propylamine; triethylamine; triethanolamine; piperidine; cyclohexylamine; 2-methylpyridine; N,N-dimethylbenzylamine; N-N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The phosphorus source is preferably phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reactive ferrous or ferric ions. Advantageously iron salts, oxides or hydroxides are employed such as iron sulfate, iron acetate, iron nitrate, or the like. Other sources such as a freshly precipitated iron oxide $\gamma$-FeOOH, are also suitable.

While not essential to the synthesis of FAPO compositions, it has been found that in general, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization the FAPO product is isolated and advantageously washed with water and dried in air. The as-synthesized FAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular FAPO species. As a general rule, the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the FAPO phase wherein the organic moiety occupying the intracrystalline pore system as a result of the hydrothermal crystallization process has been reduced by post-synthesis treatment such that the value of "m" in the composition formula:

$$mR:(Fe_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized FAPO material.

Since the FAPO compositions are formed from $AlO_2^-$, $PO_2^+$, $FeO_2^-$ and/or $FeO_2^{-2}$ units the matter of cation exchangeability is considerably more complicated than in the case of zeolitic molecular sieves in which, ideally, there is a stoichiometric relationship between $AlO_2$ tetrahedra and charge-balancing cations. In the FAPO compositions, an $AlO_2^-$ tetrahedron can be balanced electrically either by association with a $PO_2^+$ tetrahedron or a simple cation such as an alkali metal cation, a $Fe^{+2}$ or $Fe^{+3}$ cation present in the reaction mixture, or an organic cation derived from the templating agent. Similarly an $FeO_2^-$ or $FeO_2^{-2}$ tetrahedron can be balanced electrically by association with $PO_2^+$ tetrahedron, a $Fe^{+2}$ or $Fe^{+3}$ cation, organic cations derived from the templating agent, or other metal cation introduced from an extraneous source. It has also been postulated that non adjacent $AlO_2^-$ and $PO_2^+$ tetrahedral pairs can be balanced by $Na^+$ and $OH^-$, respectively [Flanigen and Grose, Molecular Sieve Zeolites-I, ACS, Washington, D.C. (1971)].

TAPO MOLECULAR SIEVES

TAPO molecular sieves are disclosed in U.S. Pat. No. 4,500,561, incorporated herein by reference, and comprise a three-dimensional microporous crystal framework structure of $[TiO_2]$, $[AlO_2]$ and $[PO_2]$ tetrahedral units which has a unit empirical formula on an anhydrous basis of:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0, the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, representing the following values for "x", "y" and "z":

|       | Mole Fraction |      |       |
|-------|---------------|------|-------|
| Point | x             | y    | z     |
| A     | 0.001         | 0.45 | 0.549 |
| B     | 0.88          | 0.01 | 0.11  |
| C     | 0.98          | 0.01 | 0.01  |
| D     | 0.29          | 0.70 | 0.01  |
| E     | 0.001         | 0.70 | 0.299 |

The parameters "x", "y" and "z" are preferably within the following values for "x", "y" and "z":

|       | Mole Fraction |       |       |
|-------|---------------|-------|-------|
| Point | x             | y     | z     |
| A     | 0.002         | 0.499 | 0.499 |
| b     | 0.20          | 0.40  | 0.40  |
| c     | 0.20          | 0.50  | 0.30  |
| d     | 0.10          | 0.60  | 0.30  |
| e     | 0.002         | 0.60  | 0.398 |

The titanium-containing molecular sieves are referred to hereinafter, solely for point of reference herein as "TAPO" molecular sieves, or as "TAPOs" if the reference is to the class as a whole. This designation is simply made for the sake of convenient reference herein and is not meant to designate a particular structure for any given TAPO molecular sieve. The members of the class of TAPOs employed hereinafter in the examples will be characterized simply by referring to such members as TAPO-5, TAPO-11, etc., i.e., a particular species will be referred to as TAPO-n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the $[TiO_2]$, $[PO_2]$ and $[AlO_2]$ tetrahedral unit within a titanium-containing molecular sieve and which forms the molecular framework of the TAPO composition(s).

The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and phosphorus.

The unit empirical formula for a TAPO may be given on an "as-synthesized" basis or may be given after an "as-synthesized" TAPO composition has been subjected to some post treatment process, e.g., calcination. The term "as-synthesized" herein shall be used to refer to the TAPO composition(s) formed as a result of the hydrothermal crystallization but before the TAPO composition has been subjected to post-treatment to remove any volatile components present therein. The actual value of "m" for a post treated TAPO will depend on several factors (including: the particular TAPO, template, severity of the post-treatment in terms of its ability to remove the template from the TAPO, the proposed application of the TAPO composition, etc.) and the value for "m" can be within the range of values as defined for the as-synthesized TAPO compositions although such is generally less than the as-synthesized TAPO unless such post-treatment process adds template to the TAPO so treated. A TAPO composition which is in the calcined or other post-treatment form generally has an empirical formula represented by Formula (1), except that the value of "m" is generally less than about 0.02. Under sufficiently severe post-treatment conditions, e.g., roasting in air at high temperature for long periods (over 1 hr.), the value of "m" may be zero (0) or, in any event, the template, R, is undetectable by normal analytical procedures.

The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to designate the spatial arrangement of the primary bond linkages. A lack of change in the framework topology indicates that there is no disruption of these primary bond linkages.

The TAPO molecular sieves are generally synthesized by hydrothermal crystallization from a reaction mixture comprising reactive sources of titanium, aluminum and phosphorus, and one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under the autogenous pressure, at a temperature of at least about 100° C., and preferably between 100° C. and 250° C., until crystals of the molecular sieve product are obtained, usually for a period of from 2 hours to 2 weeks. While not essential to the synthesis of the TAPO molecular sieves, it has been found that in general stirring or other moderate agitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO(s) may be isolated and washed with water and dried in air. As a result of the hydrothermal crystallization, the as-synthesized TAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed TAPO and may be removed by a post-treatment process, such as by calcining the TAPO at temperatures of between about 200° C. and to about 700° C. so as to thermally degrade the template or by employing some other post-treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

The TAPOs are preferably formed from a reaction mixture having a mole fraction of alkali metal cation which is sufficiently low that it does not interfere with the formation of the TAPO composition. The TAPO compositions are generally formed from a reaction mixture containing reactive sources of $TiO_2$, $Al_2O_3$, and $P_2O_5$ and an organic templating agent, said reaction mixture comprising a composition expressed in terms of molar oxide ratios of:

$$fR_2O:(Ti_xAl_yP_z)O_2:g\ H_2O$$

wherein "R" is an organic templating agent; "f" has a value large enough to constitute an effective amount of "R" said effective amount being that amount which form said TAPO compositions; "g" has a value of from zero to 500; "x", "y" and "z" represent the mole fractions, respectively, of titanium, aluminum and phosphorus in the $(Ti_xAl_yP_z)O_2$ constituent, and each has a value of at least 0.001 and being within the following values for "x", "y" and "z":

|       | Mole Fraction | | |
|-------|-------|-------|-------|
| Point | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Although the TAPO compositions will form if higher concentrations of alkali metal cation are present, such reaction mixtures are not generally preferred. A reaction mixture, expressed in terms of molar oxide ratios, comprising the following bulk composition is preferred:

$$oR_2O:wM_2O:(Ti_xAl_yP_z)O_2:nH_2O$$

wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively, of titanium, aluminum and phosphorus in $(Ti_xAl_yP_z)O_2$ "x", "y" and "z" represent the mole fractions, respectively of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presence of alkali metal cations is not preferred, when they are present in the reaction mixture it is preferred to first admix at least a portion (e.g., at least about 10 weight percent) of each of the aluminum and phosphorus sources in the substantial absence (e.g., preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously [PO2] tetrahedra for [SiO2] tetrahedra in zeolitic structures). Although the reaction mechanism is by no means clear at this time, the function of the template may be to favor the incorporation of [PO2] and [AlO2] tetrahedra in the framework structures of the crystalline products with [TiO2] tetrahedra isomorphously replacing [PO2] tetrahedra.

The reaction mixture from which these TAPOs are formed contains one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula R4X+ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in "R" of group of the template. Nitrogen-containing templates are preferred, including amines and quaternary ammonium compounds, the latter being represented generally by the formula R'4N+ wherein each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and triamines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tri-propylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine; N-methylethanolamine; N-methylcyclohexylamine; 3-methyl pyridine; 4-methylpyridine; quinuclidine; N,N'-dimethyl-1,4-diazabicyclo (2,2,2) octane ion; di-n-butylamine, neopentylamine; di-n-pentylamine; iso-propylamine; t-butylamine; ethylenediamine; pyrrolidine; and 2-imidazolidone. As will be readily apparent from the illustrative examples set forth hereinafter, not every template will produce every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TAPOs, although such may be acting as templates.

Alkali metal cations, if present in the reaction mixture, may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as structural cations balancing net negative charges at various sites in the crystal lattice. It should be understood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Most any reactive titanium source may be employed herein. The preferred reactive titanium sources include titanium alkoxides, water-soluble titanates and titanium chelates.

Most any reactive phosphorous source may be employed. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophosphates such as the AlPO4 compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained).

Organic phosphorus compounds, e.g., esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but as generally not preferred.

Since the exact nature of the TAPO molecular sieves are not clearly understood at present, although all are believed to contain [$TiO_2$] tetrahedra in the three-dimensional microporous crystal framework structure, it is advantageous to characterize the TAPO molecular sieves by means of their chemical composition. This is due to the low level of titanium present in certain of the TAPO molecular sieves prepared to date which makes it difficult to ascertain the exact nature of the interaction between titanium, aluminum and phosphorus. As a result, although it is believed that titanium, [$TiO_2$], has substituted isomorphously for [$AlO_2$] or [$PO_2$] tetrahedra, it is appropriate to characterize certain TAPO compositions by reference to their chemical composition in terms of the mole ratios of oxides in the as-synthesized and anhydrous form as:

$$vR:pTiO_2:gAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium, alumina and phosphorus pentaoxide, based on said moles being such that they are within the following values for "p", "q" and "r":

| Point | Mole Fraction | | |
|---|---|---|---|
| | p | q | r |
| A | 0.004 | 1.0 | 1.22 |
| B | 176 | 1.0 | 11.0 |
| C | 196 | 1.0 | 1.0 |
| D | 0.828 | 1.0 | 0.0143 |
| E | 0.003 | 1.0 | 0.427 |

The parameters "p", "q" and "r" are preferably within the following values for "p", "q" and "r":

| Point | Mole Fraction | | |
|---|---|---|---|
| | p | q | r |
| a | 0.008 | 1.0 | 1.0 |
| b | 1.0 | 1.0 | 1.0 |
| c | 0.80 | 1.0 | 0.60 |
| d | 0.333 | 1.0 | 0.50 |
| e | 0.067 | 1.0 | 0.663 |

ELAPO MOLECULAR SIEVES

"ELAPO" molecular sieves are a class of crystalline molecular sieves in which at least one element capable of forming a three-dimensional microporous framework form crystal framework structures of $AlO_2^-$, $PO_2^+$ and $MO_2^n$ tetrahedral oxide units wherein "$MO_2^n$" represents at least one different element (other than Al or P) present as tetrahedral oxide units "$MO_2^n$" with charge "n" where "n" may be −3, −2, −1, 0 or 30 1. The members of this novel class of molecular sieve compositions have crystal framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2^-$ and $PO_2^+$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc. ELAPOs and their preparation are disclosed in European patent application Ser. No. 85104386.9, filed Apr. 11, 1985 (EPC Publication No. 0158976, published October 13, 1985, incorporated herein by reference) and 85104388.5, filed Apr. 11, 1985 (EPC Publication No. 158349, published Oct. 16, 1985, incorporated herein by reference).

The ELAPO molecular sieves are generally referred to herein by the acronym or "ELAPO" to $AlO_2^-$, $PO_2^+$ and $MO_2^n$ tetrahedral oxide units. Actual class members will be identified by replacing the "EL" of the acronym with the elements present as $MO_2^N$ tetrahedral units. For example, "MgBeAPO" designates a molecular sieve comprised of $AlO_2^-$, $PO_2^+$, $MgO_2^{-2}$ and $BeO_2^{-2}$ tetrahedral units. To identify various structural species which make up each of the subgeneric classes, each species is assigned a number and is identified as "ELAPO-i" wherein "i" is an integer. The given species designation is not intended to denote a similarity in structure to any other species denominated by a similar identification system.

The ELAPO molecular sieves comprise at least one additional element capable of forming framework tetrahedral oxide units ($MO_2^n$) to form crystal framework structures with $AlO_2^-$ and $Po_2^+$ tetrahedral oxide units wherein "M" represents at least one element capable of forming tetrahedral units "$MO_2^n$", where "n" is −3, −2, −1, 0 or +1 and is at least one element selected from the group consisting of arsenic, beryllium, boron, chromium, gallium, germanium and lithium. When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2^-$, $PO_2^+$ and $MO_2^n$ tetrahedral units and have an empirical chemical composition on an anhydrous basis expressed by the formula:

mR:$(M_xAl_yP_z)O_2$;

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

mR:$(M_xAl_yP_z)O_2$ where "x", "y" and "z" represent the mole fractions of said "M", aluminum and phosphorus. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, etc. for "M" as above defined. The values of "$x_1$", "$x_2$", "$x_3$", etc. are as defined for "x", hereinafter, where "$x_1$"+"$x_2$"+"$x_3$" ... ="x" and where $x_1$, $x_2$, $x_3$, etc. are each at least 0.01.

The ELAPO molecular sieves have crystalline three dimensional microporous framework structures of $MO_2^n$, $AlO_2^-$ and $PO_2^+$ units having an empirical chemical composition on an anhydrous basis expressed by the formula:

mR:$(M_xAl_yP_z)O_2$ wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub class of the ELAPOs of this invention, the values of "x", "y" and "z" in the formula above are within the following values for "x", "y" and "z":

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorus, preferably an organic templating, i.e., structure directing, agent, preferably a compound of an element of Group VA of the Periodic Table, and-/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is preferred to employ a reaction mixture composition expressed in terms of the molar ratios as follows:

aR:$(M_xAl_yP_z)O_2$:b$H_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2^n$, with $AlO_2^-$ and $PO_2^+$ tetrahedral units; "n" has a value of −3, −2, −1, 0 or +1; and "x", "y" and "z" represent the mole fractions of "M", aluminum and phosphorus, respectively, "y" and "z" each have a value of at least 0.01 and "x" has a value of at least 0.01 with each element "M" having a mole fraction of at least 0.01. The mole fractions "x", "y" and "z" are preferably within the following values for "x", "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0 39 | 0.60 | 0.01 |

In the foregoing expression of the reaction composition, the reactants are normalized with respect to a total of $(M+Al+P)=(x+y+z)=1.00$ mole, whereas in many of the working examples appearing hereinafter the reaction mixtures are expressed in terms of molar oxide ratios and may be normalized to 1.00 mole of $P_2O_5$. This latter form is readily converted to the former form by routine calculations by dividing the total number of moles of "M", aluminum and phosphorus into the moles of each of "M", aluminum and phosphorus. The moles of template and water are similarly normalized by dividing the total moles of "M", aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n propylamine; tripropylamine; triethylamine; triethanolamine; piperidine; cyclohexylamine; 2-methylpyridine; N,N dimethylbenzylamine; N,N dimethylethanolamine; choline; N,N'-dimethylpiperazine; 1,4-diazabicyclo (2,2,2,) octane; N methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n butylamine, neopentylamine; di-n-pentylamine; isopropylamine; t-butylamine; ethylenediamine; pyrrolidine; and 2-imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents.

The phosphorus source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organo phosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxylates, may be employed including the chlorides, bromides, iodides, nitrates, sulfates, acetates, formates, ethoxides, propoxides and the like.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, aluminosilicate or molecular sieve compositions, facilitates the crystallization procedure.

After crystallization the ELAPO product may be isolated and advantageously washed with water and dried in air. The as-synthesized ELAPO generally contains within its internal pore system at least one form of the templating agent employed in its formation. Most commonly the organic moiety is present, at least in part, as a charge balancing cation as is generally the case with as-synthesized aluminosilicate zeolites prepared from organic containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

has a value of less than 0.02. The other symbols of the formula are as defined hereinabove. In those preparations in which an alkoxide is employed as the source of element "M", aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized ELAPO material.

Since the present ELAPO compositions are formed from $MO_2^n$, $AlO_2$, and $PO_2^+$ tetrahedral oxide units which, respectively, have a net charge of "n", (where "m" may be $-3$, $-2$, $-1$, 0 or $+1$, $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of "M" present in the reaction mixture, or an organic cation derived from the templating agent. Similarly an $MO_2^n$ tetrahedron, where "n" is negative, can be balanced electrically by association with $PO_2^+$ tetrahedra, a cation of "M" present in the reaction mixture, organic cations derived from the templating agent, a simple cation such as an alkali metal cation, or other divalent or polyvalent metal cation, a proton ($H^+$), anions or cations introduced from an extraneous source. It has also been postulated that non adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)]

DISCUSSION OF PROCESS

The term "light olefins" will be used hereinafter to refer to olefins having two to four carbon atoms, inclusive. Although other hydrocarbon products are formed, the products of particular interest herein are the light olefins and they are preferably produced as the major hydrocarbon products, i.e., over 50 mole percent of the hydrocarbon product is light olefins.

It has been discovered that the instant non-zeolitic molecular sieves can provide selectivity to $C_2$ to $C_4$ olefin products (i.e., ethylene, propylene, and butenes) of at least about 25 molar percent, based on the total hydrocarbon products formed, may be obtained, preferably in excess of 50 mole percent. Further, high molar conversions, i.e., preferably at least about 70 percent and most preferably at least about 90 percent, based on the moles of feedstock to products, are believed obtainable while forming a minimum molar amount of methane (less than about ten (10) molar percent and preferably less than about five (5) molar percent) and while forming only minor amounts of saturated hydrocarbons and $C_5$ and higher hydrocarbons (typically less than about 10 molar percent).

The instant process provides improved ethylene to propylene molar ratios by carrying out the process in the presence of a diluent correlated to the selected NZMS.

The instant process employs a feedstock comprising "aliphatic hetero compounds". The term "aliphatic hetero compounds" is employed herein to include alcohols, halides, mercaptans, sulfides, amines, ethers and carbonyl compound (aldehydes, ketones, carboxylic acids, esters and the like). The aliphatic moiety preferably contains from 1 to about 10 carbon atoms and more preferably contains from 1 to about 4 carbon atoms. Suitable reactants include lower straight and branched (of appropriate size) chain alkanols, their unsaturated counterparts, and the nitrogen halogen and sulfur analogue of such. Representative of suitable aliphatic hetero compounds include: methanol; methyl chloride, methyl mercaptan; methyl sulfide; methyl amines; dimethyl ether; ethanol; ethyl mercaptan; ethyl chloride; diethyl ether; methylethyl ether; formaldehyde; dimethyl ketone; acetic acid; n-alkyl amines; n-alkyl halides and n-alkyl sulfides having n-alkyl group having 3 to 10 carbon atoms; and mixtures thereof.

The instant process is preferably carried out in the vapor phase such that the feedstock is contacted in a vapor phase in a reaction zone with a non zeolitic molecular sieve at effective process conditions such as to produce light olefins, i.e., an effective temperature, pressure, WHSV (Weight Hourly Space Velocity) and with an effective amount of diluent to produce light olefins. Alternatively, the process may be carried out in a liquid phase. When the process is carried out in the liquid phase the process necessarily involves the separation of products formed in a liquid reaction media and can result in different conversions and selectivities of feedstock to product with respect to the relative ratios of the liqht olefin products as compared to that formed by the vapor phase process.

The temperature which may be employed in the process may vary over a wide range depending, at least in part, on the selected NZMS catalyst. In general, the process can be conducted at an effective temperature between about 200° C. and about 700° C., preferably between about 250° C. and about 600° C., and most preferably between about 300° C. and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. and about 700° C.

The process is effectively carried out over a wide range of pressures including autogenous pressures. At pressures between about 0.001 atmospheres and about 1000 atmospheres, the formation of light olefin products will be effected although the optimum amount of product will not necessarily form at all pressures. The preferred pressure is between about 0.01 atmospheres and about 100 atmospheres. The pressures referred to herein for the process are exclusive of the diluent, and refer to the partial pressure of the feedstock as it relates to the aliphatic hetero compounds and/or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum, although light olefin products can be formed.

The process is effected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the non zeolitic molecular sieve selected, the WHSV, the phase (liquid or vapor) selected, and, perhaps, selected process design characteristics.

The process is effectively carried out over a wide range of WHSV for the feedstock and is generally between about 0.01 hr$^{-1}$ 100 hr$^{-1}$ and preferably between about 0.1 hr$^{-1}$ and about 40 hr$^{-1}$. Values above 100 hr$^{-1}$ employed and are intended to be covered by the instant process, although such are not preferred.

The instant process is most preferably carried out under process conditions comprising a temperature between about 300° C. and about 500° C., a pressure between about 0.1 atmosphere (one atmosphere equals 14.7 psia) to about 100 atmospheres, utilizing a WHSV expressed in hr$^{-1}$ for each component of the feedstock having a value between about 0.1 and about 40. The temperature, pressure, and WHSV are each selected such that the effective process conditions, i.e., the effective temperature, pressure, and WHSV, are employed in conjunction, i.e., correlated, with the selected non zeolitic molecular sieve and selected feedstock such that light olefin products are produced.

The selection of the diluent is preferably such that the diluent is correlated to the selected NZMS such that the average kinetic diameter of the diluent molecules is greater than the average pore size of the non-zeolitic molecular sieve. The selection of the diluent is also related to the relative stability of the diluent under the process conditions. The average pore sizes of the NZMSs are such that the diluent is generally one or more cyclic compounds having 5 or more atoms in the ring, e.g., cycloalkanes, cycloalkenes, pyridine and aromatic compounds. The diluent should be thermally stable under the process conditions. Aromatic compounds employable herein include compounds of the formula:

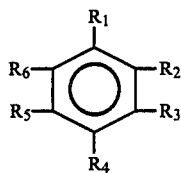

wherein $R_1$, $R_2$, $R_3$, $R_4$, $R_5$, $R_6$ may be alkyl, alkylaryl, araalkyl, aryl and mixtures thereof, containing 1 to 20 carbon atoms and optionally, hetero atoms (S, N, Cl, etc.). The diluent may be selected from the group consisting of: cycloalkanes and substituted cycloalkanes (cyclopentane, cyclohexane); pyridine and substituted pyridine; benzene; alkyl benzenes including toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene; biphenyl, diphenylmethane; triphenylmethane; 1,2-diphenylethane; anthracene; naphthalene; and the like.

In addition to the presence of the diluent that is correlated to the selected NZMS as above described, which may be present in an amount between about 1 and about 99 weight percent of the feedstock, and the aliphatic hetero compound(s) in the feedstock, other diluents may be present in the feedstock in place of such diluent in an amount between about 1 and about 80 molar percent, based on the total number of moles of all feed and diluent components fed to the reaction zone (or catalyst). Typical of additional diluents which may be employed in the instant process are helium, argon, nitrogen, carbon monoxide, carbon dioxide, hydrogen, water(steam), paraffins, hydrocarbons (such as methane and the like), mixtures thereof, and the like.

It has been discovered that the addition of a diluent (correlated to the pore sizes of the selected NZMS), e.g., aromatic diluent, to a feedstock comprising aliphatic hetero compounds is beneficial in increasing the molar ratio of ethylene to propylene in the hydrocarbon products. In many processes where ethylene is the desired light olefin this increase in the relative amount of ethylene may be of significant commercial importance.

The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such non-zeolitic molecular sieves in series to provide for a desired product mixture. Owing to the nature of the process, it may be desirous to carry out the instant process by use of the NZMSs in a dynamic (e.g., fluidized or moving) bed system or any system of a variety of transport beds rather than in a fixed bed system. Such systems would readily provide for any regeneration (if required) of the non zeolitic molecular sieve catalyst after a given period of time. If regeneration is required, the non zeolitic molecular sieve catalyst can be continuously introduced as a moving bed to a regeneration zone where it can be regenerated, such as for example by removing carbonaceous materials by oxidation in an oxygen-containing atmosphere. In the preferred practice of the invention, the catalyst will be subject to a regeneration step by burning off carbonaceous deposits accumulated during reactions.

NON-ZEOLITIC MOLECULAR SIEVE CATALYSTS

The selection of the non-zeolitic molecular sieve catalysts for the instant process is preferably related, in part, to the desired product mixture sought to be obtained. The selected non-zeolitic molecular sieve desirably has a kinetic pore diameter (average kinetic diameter in Angstroms, Å) such that the selectivity to the light olefin products is greater than 50 molar percent. Accordingly, at least a portion, preferably a major portion, of the pores have an average kinetic diameter characterized such that the adsorption capacity (as measured by the standard McBain-Bakr gravimetric adsorption method using given adsorbate molecules) shows adsorption of oxygen (average kinetic diameter of about 3.46Å) and negligible adsorption of isobutane (average kinetic diameter of about 5.0Å). More preferably the average kinetic diameter is characterized by adsorption of Xenon (average kinetic diameter of about 4.0Å) and negligible adsorption of isobutane and most preferably by adsorption of n-hexane (average kinetic diameter of about 4.3Å) and negligible adsorption of isobutane. Negligible adsorption of oxygen or xenon is adsorption of less than four percent by weight of the adsorbate based on the weight of the GZMS and adsorption of oxygen or xenon is adsorption of greater than or equal to four percent by weight of the adsorbate based on the weight of the NZMS. Negligible adsorption of n-hexane or isobutane is adsorption of less than two percent by weight of the adsorbate based on the weight of the NZMS and adsorption of n hexane or isobutane is adsorption of greater than or equal to two percent by weight of the adsorbate based on the weight of the NZMS. Although it is clear that factors other than just the kinetic pore size will affect the products formed, including any occlusion of the pores, the exact nature of such other factors or their exact effect on the products formed are not understood at present. It is believed that the kinetic diameter of the pores of the non zeolitic molecular sieve is related to the products formed. Although a specific NZMS may not have a kinetic pore diameter within the desired or preferred range the NZMS may be modified by depositing or impregnating such with cations, anions, salts and/or compounds that occlude or otherwise result in the modification of a NZMS having a large pore size to one having a kinetic pore diameter(s) within the desired or preferred range.

Techniques which may be employed to effect the diminution of the pore size of a non-zeolitic molecular sieve are generally known in the art. Such procedures generally involve the introduction to a pore of a pore size restricting material and may involve such procedures as (1) impregnating the NZMS with a solution comprising a solvent or solubilizing agent for such a pore restricting material (one or more)in an amount sufficient to deposit the desired weight of such pore restricting material to the NZMS such that the desired pore size is obtained and/or (2) exchanging the NZMS with a solution containing the pore size restricting material. The impregnation or deposition of the pore restricting materials may be generally accomplished by heating the NZMS at an elevated temperature to evaporate any liquid present to effect deposition or impregnation of the pore restricting material into the interior and/or onto the exterior surface of the NZMS, or by the exchange of cations present in the NZMS with cations that provide for the desired kinetic pore size. Alternatively, the pore restricting material may be formed on the NZMS from an emulsion or slurry containing the pore restricting material by heating the NZMS as described above. Impregnation and exchange procedures are generally the preferred techniques because they utilize and introduce the pore restricting material more efficiently than other procedures such as coating procedures since a coating procedure is generally not able to effect substantial introduction of the pore restricting material onto the interior surfaces of the NZMS. In addition, coated materials are more generally susceptible to the loss of the pore restricting materials by abrasion.

Suitable pore restricting materials include alkali metal, alkaline earth metals, transition metals and the salts thereof including inorganic and organic salts such as: nitrates, halides, hydroxides, sulfates and carboxylates. Other pore restricting materials generally employed in the art for such are also believed to be employable herein.

In carrying out the instant process the NZMS molecular sieves may be admixed (blended) or provided sequential to other materials which may provide some property which is beneficial under process conditions, such as improved temperature resistance or improved catalyst life by minimization of coking or which is simply inert under process conditions. Such materials may include synthetic or naturally occurring substances as well as inorganic materials such as clays, silicas, aluminas, crystalline aluminosilicate zeolites, metal oxides and mixtures thereof. In addition, the non zeolitic molecular sieves may be formed with materials such as silica, alumina, silica-alumina, silica-magnesia, silico-zirconia, silica-thoria, silica-berylia, silica-titania, as well as ternary compositions, such as silica-alumina-thoria, silica-alumina-zirconia and clays present as binders. The relative proportions of the above materials and the NZMS may vary widely with NZMS content ranging between about 1 and about 99 percent by weight of the composite.

EXPERIMENTAL PROCEDURE (LIGHT OLEFIN PRODUCTION)

The production of light olefins in the examples was carried out by mixing about 0.5 gram of a selected NZMS with 2.5 grams of quartz chips (20-30 U.S. Standard mesh). The resulting mixture was then placed in a 1/4 inch (outside diameter) No. 304 stainless steel tubular reactor having a wall thickness of 0.035 inch. The tubular reactor was immersed in a fluidized heated sand bath having electrical resistance heaters provided for maintaining the sand bath and the tubular reactor at the desired temperature. Thermocouples were provided for measurement of the reactor temperature.

A selected feedstock was introduced to the tubular reactor by means of a Model 100 Altex Metering Pump (from Altex Corporation, a subsidiary of the Beckmann Corporation) concurrently with a stream of diluent with nitrogen and water (steam) being employed as diluents (unless otherwise noted in the examples hereinafter). The pressure employed in the examples was the autogenous pressure about one (1) to about two (2) atmospheres unless otherwise noted. The ratios of feedstock components are reported as weight ratios. Nitrogen was employed as a diluent and was introduced at a flow rate of about 5 cubic centimeters per minute.

The effluent from the tubular reactor (the reaction products) was analyzed. The liquid component of the effluent was collected at room temperature and subsequently analyzed by vapor phase chromatography, whereas the gaseous component of the effluent was sampled and analyzed directly from the effluent stream by vapor phase chromatography.

The analyses of both the liquid and vapor components of the effluent from the tubular reactor were carried out by programmed temperature chromatography having a thermal conductivity detector with a programmed increase in the chromatographic column's temperature over the chromatographic analysis. The analysis of the liquid and vaporous components of the effluent, including the analysis of all standards was carried out using chromatographic techniques by use of the following chromatographic instruments:

|  | Phase Analyzed | |
| --- | --- | --- |
|  | Liquid | Vapor |
| Chromatograph Column | Varian 3700 20 feet × ⅛ inch (O.D.) stainless steel | Hewlett Packard 11 feet × ⅛ inch (O.D.) stainless steel |
| Packing | 10% Carbowax Chrom T 60/80 mesh | Porapak R |

Unless otherwise noted, the Molar Conversion to total products, based on methanol ethanol, dimethyl ether, diethyl ether or mixtures thereof, was 100% with the Molar Efficiency to a particular product being given as a percentage. When a product was not detected (ND) or if only a trace amount was qualitatively detected such is reported as ND or Trace (TR), respectively. The NZMSs employed in the following example are denominated according to the nomenclature of the above mentioned applications. The NZMSs of particular interest in the aforementioned applications are those denominated therein by a "−n" designation where "n" is 17, 34, 35, 44 and 47. The NZMSs were calcined prior to their use in the examples. The following examples are provided to exemplify the invention and are not meant to be limiting in any way.

PRODUCTION OF LIGHT OLEFINS: EXAMPLES

Examples 1 to 9

NZMSs were employed as the catalyst for the conversion of methanol to light olefins. The feedstock was a 70/30 by weight mixture of water to methanol. In each case nitrogen was added at a flow rate of about 5 cc/minute. The data in the Tables I to IX show that the NZMSs are effective in converting methanol to light olefin products.

TABLE I (MAPO-34)[1]

|  | Molar Selectivity, % | |
|---|---|---|
|  | 375° C. | 425° C. |
| Ethylene | 40.1 | 45.7 |
| Ethane | 1.5 | 0.9 |
| Propylene | 33.3 | 29.2 |
| Propane | 1.1 | TR |
| Butenes | 8.4 | 8.5 |
| $C_5$ | 1.2 | 1.6 |
| $C_6$ | TR | TR |
| Methane | 5.9 | 6.2 |
| Carbon Dioxide | 8.5 | 7.6 |
| Dimethyl Ether | — | 0.3 |
| $C_2$–$C_4$ Olefins | 81.8 | 83.4 |
| $C_2/C_3$ | 1.20 | 1.57 |
| WHSV (Methanol), $hr^{-1}$ | 0.90 | 1.12 |
| Run Time, hr | 4.0 | 5.5 |

[1]MAPO-34 is disclosed in U.S. Pat. No. 4,567,029.

TABLE II (MAPO-35)[1]

|  | Molar Selectivity, % | |
|---|---|---|
|  | 375° C. | 425° C. |
| Ethylene | 52.1 | 47.7 |
| Ethane | 0.5 | 0.5 |
| Propylene | 27.3 | 26.8 |
| Propane | ND | ND |
| Butenes | 4.7 | 5.4 |
| $C_5$ | 3.1 | 1.7 |
| $C_6$ | TR | TR |
| Methane | 10.6 | 13.3 |
| Carbon Dioxide | 1.7 | 4.6 |
| $C_2$–$C_4$ Olefins | 84.2 | 79.9 |
| $C_2/C_3$ | 1.91 | 1.78 |
| Methanol Conversion, % | 63.0 | 71.0 |
| Dimethyl Ether Yield, % | 26.9 | 7.6 |
| WHSV (Methanol), $hr^{-1}$ | 0.78 | 1.00 |
| Run Time, hr | 1.0 | 0.5 |

[1]MAPO-35 is disclosed in U.S. Pat. No. 4,567,029.

TABLE III (CoAPSO-34)

|  | Molar Selectivity, % | |
|---|---|---|
|  | 375° C. | 425° C. |
| Ethylene | 38.1 | 46.8 |
| Ethane | 0.8 | 0.5 |
| Propylene | 36.0 | 23.2 |
| Propane | TR | ND |
| Butenes | 9.2 | 5.4 |
| $C_5$ | 1.4 | 1.3 |
| $C_6$ | 0.1 | 0.4 |
| Methane | 3.8 | 8.3 |
| Carbon Dioxide | 10.6 | 13.9 |
| Dimethyl Ether | TR | TR |
| $C_2$–$C_4$ Olefins | 83.4 | 75.4 |
| $C_2/C_3$ | 1.06 | 2.02 |
| WHSV (Methanol), $hr^{-1}$ | 0.95 | 0.93 |
| Run Time, hr | 2.5 | 4.8 |

TABLE IV (CoAPO-34)[1]

|  | Molar Selectivity, % | |
|---|---|---|
|  | 375° C. | 425° C. |
| Ethylene | 37.7 | 45.3 |
| Ethane | 2.3 | 0.8 |
| Propylene | 38.6 | 27.1 |
| Propane | TR | TR |
| Butenes | 12.9 | 8.3 |
| $C_5$ | 3.2 | 1.4 |
| $C_6$ | 1.1 | 0.8 |
| Methane | 2.4 | 6.2 |
| Carbon Dioxide | 1.7 | 10.0 |
| Dimethyl Ether | ND | ND |
| $C_2$–$C_4$ Olefins | 89.2 | 80.7 |
| $C_2/C_3$ | 0.98 | 1.67 |
| WHSV (Methanol), $hr^{-1}$ | 0.96 | 0.94 |
| Run Time, hr | 1.0 | 4.8 |

[1]CoAPO-34 is disclosed in U.S. Pat. No. 4,567,029.

TABLE V (TiAPSO-34)

|  | Molar Selectivity, % | |
|---|---|---|
|  | 375° C. | 425° C. |
| Ethylene | 44.6 | 53.5 |
| Ethane | 0.9 | 0.9 |
| Propylene | 40.4 | 29.1 |
| Propane | ND | ND |
| Butenes | 9.9 | 5.6 |
| $C_5$ | 1.6 | 0.7 |
| $C_6$ | 0.1 | 0.1 |
| Methane | 1.6 | 4.2 |
| Carbon Dioxide | 0.9 | 5.8 |
| Dimethyl Ether | TR | TR |
| $C_2$–$C_4$ Olefins | 94.9 | 88.3 |
| $C_2/C_3$ | 1.10 | 1.84 |
| WHSV (Methanol), $hr^{-1}$ | 0.98 | 0.83 |
| Run Time, hr | 6.3 | 10.0 |

TABLE VI (MgAPSO-34)

|  | Molar Selectivity, % | |
|---|---|---|
|  | 375° C. | 425° C. |
| Ethylene | 41.9 | 50.0 |
| Ethane | 0.6 | 0.6 |
| Propylene | 40.3 | 28.5 |
| Propane | ND | ND |
| Butenes | 11.7 | 7.4 |
| $C_5$ | 2.1 | 1.3 |
| $C_6$ | 0.2 | 0.1 |
| Methane | 1.8 | 5.6 |
| Carbon Dioxide | 1.3 | 6.5 |
| Dimethyl Ether | TR | ND |
| $C_2$–$C_4$ Olefins | 93.9 | 86.0 |
| $C_2/C_3$ | 1.04 | 1.76 |
| WHSV (Methanol), $hr^{-1}$ | 0.92 | 0.91 |

TABLE VI-continued

(MgAPSO-34)

| | Molar Selectivity, % | |
|---|---|---|
| | 375° C. | 425° C. |
| Run Time, hr | 4.0 | 7.0 |

TABLE VII

(MgAPSO-35)

| | Molar Selectivity, % 425° C. |
|---|---|
| Ethylene | 44.1 |
| Ethane | 2.6 |
| Propylene | 21.0 |
| Propane | TR |
| Butenes | 5.7 |
| $C_5$ | 2.5 |
| $C_6$ | 0.7 |
| Methane | 13.9 |
| Carbon Dioxide | 9.4 |
| Dimethyl Ether | ND |
| $C_2$-$C_4$ Olefins | 70.8 |
| $C_2/C_3$ | 2.1 |
| WHSV (Methanol), hr$^{-1}$ | 0.92 |
| Run Time, hr | 1.0 |

TABLE VIII

(MnAPO-34)[1]

| | Molar Selectivity, % 425° C. |
|---|---|
| Ethylene | 43.6 |
| Ethane | 0.6 |
| Propylene | 31.1 |
| Propane | ND |
| Butenes | 10.4 |
| $C_5$ | 1.7 |
| $C_6$ | 0.2 |
| Methane | 4.7 |
| Carbon Dioxide | 7.6 |
| Dimethyl Ether | TR |
| $C_2$-$C_4$ Olefins | 85.1 |
| $C_2/C_3$ | 1.40 |
| WHSV (Methanol), hr$^{-1}$ | 0.92 |
| Run Time, hr | 3.3 |

[1] MnAPO-34 is disclosed in U.S. Pat. No. 4,567,029.

TABLE IX

(ZnAPSO-34)

| | Molar Selectivity, % | |
|---|---|---|
| | 375° C. | 425° C. |
| Ethylene | 40.6 | 51.3 |
| Ethane | 0.2 | 0.1 |
| Propylene | 41.3 | 30.6 |
| Propane | ND | ND |
| Butenes | 14.6 | 11.4 |
| $C_5$ | 1.6 | 0.9 |
| $C_6$ | 0.1 | 0.1 |
| Methane | 1.3 | 4.0 |
| Carbon Dioxide | 0.2 | 1.5 |
| Dimethyl Ether | TR | TR |
| $C_2$-$C_4$ Olefins | 96.5 | 93.3 |
| $C_2/C_3$ | 0.98 | 1.67 |
| WHSV (Methanol), hr$^{-1}$ | 0.92 | 0.92 |
| Run Time, hr | 2.0 | 3.5 |

What is claimed is:

1. A process for selectively making light olefins containing 2 to 4 carbon atoms which comprises contacting a feedstock comprising aliphatic hetero compounds and mixtures thereof with a non-zeolitic molecular sieve NZMS, selected from the group consisting of ELAPSOs, CoAPSOs, FeAPSOs, MgAPSOs, MnAPSOs, TiAPSOs, ZnAPSOs, CoMnAPSOs, CoMngAPSOs, ELAPOs, MeAPOs, TAPOs, FAPOs and mixtures thereof at effective process conditions to selectively produce light olefins.

2. The process of claim 1 wherein said process is carried out in the presence of a diluent.

3. The process of claim 1 wherein the NZMS is characterized by adsorption of oxygen and negligible adsorption of isobutane.

4. The process of claim 1 wherein the NZMS is characterized by adsorption of Xenon and negligible adsorption of isobutane.

5. The process of claim 1 wherein the NZMS is characterized by adsorption of n-hexane and negligible adsorption of isobutane.

6. The process of claim 2 for making light olefins containing 2 to 4 carbon atoms which comprises contacting a feedstock comprising aliphatic hetero compounds and mixtures thereof with a non-zeolitic molecular sieve in the presence of an aromatic diluent.

7. The process of claim 1 wherein said NZMS is selected from the group consisting of CoAPSOs, FeAPSOs, MgAPSOs, MnAPSOs, TiAPSOs, ZnAPSOs, CoMgAPSOs, CoMnMgAPSOs and mixtures thereof.

8. The process of claim 1 wherein said NZMS is selected from the group consisting of NZMSs having an "—n" designation wherein "n" is selected from the group consisting of 17, 34, 35, 44 and 47.

9. The process of claim 1 wherein said NZMS is selected from the group consisting of MAPO-34, MAPO-35, CoAPSO-34, CoAPO-34, MgAPSO 34, MgAPSO-35, MnAPSO-34, ZnAPSO-34 and mixtures thereof.

10. The process of claim 1 wherein said NZMS is selected from the group consisting of MeAPO-11, MeAPO-31, MeAPO-34, MeAPO-41, TAPO-11, TAPO-31, TAPO-34, TAPO-41, FAPO-11, FAPO-31, FAPO-41 and mixtures thereof.

11. The process of claim 10 wherein "Me" is selected from the group consisting of cobalt magnesium, manganese and mixtures thereof.

12. The process of claim 10 wherein "Me" is selected from the group consisting of magnesium, manganese and mixtures thereof.

13. The process of claim 1 wherein the aliphatic hetero compound is selected from the group consisting of alcohols, ethers, amines, mercaptans, aldehydes, ketones, halides and mixtures thereof wherein the aliphatic moiety contains from 1 to about 10 carbon atoms.

14. The process of claim 6 wherein light olefins constitute at least about 25 molar percent the hydrocarbon products.

15. The process of claim 14 wherein light olefin products constitute in excess of 5% molar percent of the hydrocarbon products.

16. The process of claim 6 wherein said diluent is selected from the group consisting of cycloalkanes, pyridine and aromatic compounds of the formula:

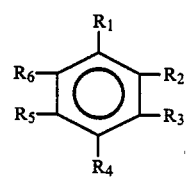

wherein $R_1$, $R_2$, $R_3$, $R_4$, $R_5$, and $R_6$ may be alkyl, araalkyl, aryl, alkylaryl or mixtures thereof containing from 1 to 20 carbon or hetero atoms.

17. The process of claim 16 wherein said aromatic diluent is selected from the group consisting of benzene, toluene, o-xylene, m-xylene, p-xylene, hemimellitene, pseudocumene, mesitylene, prehnitene, isodurene, durene, pentamethylbenzene, hexmethylbenzene, ethylbenzene, n-propylbenzene, cumene, n-butylbenzene, isobutylbenzene, sec-butylbenzene, tert-butylbenzene, p-cymene, biphenyl, diphenylmethane, triphenyl methane, anthracene; naphthalene; 1,2-diphenylethane and mixtures thereof.

18. The process of claim 1 or 6 wherein the feedstock is contacted with said NZMS at a temperature between about 200° C. and about 700° C.

19. The process of claim 18 wherein the feedstock is contacted with said NZMS at a temperature between about 250° C. and about 600° C.

20. The process of claim 1 or 6 wherein the process is conducted at a pressure between about 0.1 atmosphere and about 1000 atmospheres.

21. The process of claim 20 wherein the process is conducted at a pressure between about 0.1 atmosphere and about 100 atmospheres.

22. The process of claim 1 or 6 wherein said process is carried out in the vapor phase.

23. The process of claim 1 or 6 wherein said process is carried out in the liquid phase.

24. The process of claim 1 or 6 wherein the WHSV is between about 0.01 $hr^{-1}$ and about 100 $hr^{-1}$.

25. The process of claim 24 wherein the WHSV is between about 0.1 $hr^{-1}$ and about 40 $hr^{-1}$.

26. The process of claim 1 wherein the feedstock comprises methanol.

27. The process of claim 1 wherein the feedstock comprises methanol and dimethyl ether.

28. The process of claim 1 wherein the feedstock comprises ethanol.

29. The process of claim 1 wherein the feedstock comprises ethanol and diethyl ether.

30. The process of claim 1 wherein the feedstock consists essentially of methanol, dimethyl ether and an aromatic diluent selected from the group consisting of benzene, toluene, xylene and mixtures thereof.

31. The process of claim 1 wherein the feedstock comprises at least one of methanol, ethanol and dimethyl ether and an aromatic diluent selected from the group consisting of benzene, toluene, xylene and mixtures thereof.

32. The process of claim 1 wherein said feedstock comprises of at least one of the methanol, ethanol, and dimethyl ether, from 1 weight percent to about 99 weight percent of an aromatic diluent, at a temperature between about 200° C. and about 700° C., at a pressure between about 0.01 atmospheres and about 1000 atmospheres, at a WHSV between about 0.01 $hr^{-1}$ and about 100 $hr^{-1}$.

* * * * *